US006451341B1

(12) United States Patent
Slaga et al.

(10) Patent No.: US 6,451,341 B1
(45) Date of Patent: Sep. 17, 2002

(54) TIME RELEASE FORMULATION OF VITAMINS, MINERALS AND OTHER BENEFICIAL SUPPLEMENTS

(76) Inventors: Thomas J. Slaga, 2006 Plumbrook Dr., Austin, TX (US) 78746; Daryl L. DeLuca, 11675 W. Bellfort #1109, Houston, TX (US) 77099; William S. Sparks, 5551 Huisache, Bellaire, TX (US) 77401

(*) Notice: Subject to any disclaimer, the term of this patent is extended or adjusted under 35 U.S.C. 154(b) by 0 days.

(21) Appl. No.: 07/887,451

(22) Filed: May 22, 1992

Related U.S. Application Data

(60) Continuation-in-part of application No. 07/555,949, filed on Jul. 19, 1990, now abandoned, which is a division of application No. 07/475,641, filed on Feb. 5, 1990, now abandoned.

(51) Int. Cl.[7] .................................................. A61K 9/22
(52) U.S. Cl. ........................................ 424/468; 514/904
(58) Field of Search ............................... 424/468, 94.1, 424/94.4; 514/904, 905, 964

(56) References Cited

U.S. PATENT DOCUMENTS

| 4,022,913 | A |   | 5/1977  | Newmark ............... 424/344 |
| 4,540,584 | A |   | 9/1985  | Someya ................. 424/156 |
| 4,588,717 | A |   | 5/1986  | Mitchell ............... 514/724 |
| 4,599,234 | A | * | 7/1986  | Amer ................... 424/164 |
| 4,629,625 | A |   | 12/1986 | Gaull ................... 424/145 |
| 4,695,590 | A |   | 9/1987  | Lippman ................ 514/724 |
| 4,752,479 | A |   | 6/1988  | Briggs et al. .......... 424/472 |
| 4,863,898 | A |   | 9/1989  | Ashmead et al. ......... 514/6 |
| 4,997,852 | A |   | 3/1991  | Minton et al. .......... 514/170 |

FOREIGN PATENT DOCUMENTS

| EP | 0129032 | 12/1984 |
| EP | 0259167 | 3/1988  |

OTHER PUBLICATIONS

Slaga, et al., (1984), "Potential for Preventing Cancer by Chemical Inhibitors" *The Cancer Bulletin,* 36(1):61–4 published in USA.
Weeks, et al., (1979), "Inhibition of Phorbol Ester–Induced Tumor Promotion in Mice by Vitamin A Analog and Anti–inflammatory Steroid" *J.N.C.I.,* 63(2):401–6 published in USA.
Slaga, et al., (1980), "Studies on mechanism of Action of anti–tumor–promoting agents: Their specificity in two–stage promotion" *Proc. Natl. Acad. Sci.,* USA, (77(4):2251–4 published in USA.
Solanki, et al., (1981), "Diminution of mouse epidermal superoxide dismutase and catalase activities by tumor promoters" *Carcinogenesis,* 2:1141–6 published in England.
Slaga (1982), "Multistage Chemical Carcinogenesis in Mouse Skin" *Gann,* 9:1715–9 published in Japan.
Slaga (1981), "Food Additives and Contaminants as Modifying Factors in Cancer Induction" *Nutrition and Cancer: Etiology and Treatment,* 279–90 (Newell and Ellison, eds.) published in USA.
Slaga, et al., (1984), "Inhibition of Chemical Carcinogenesis" *Chemical Carcinogens* Second Ed., vol. 2, Chpt. 21 1279–1321 (C.E. Searle, eds.) published in USA.
Rotstein, et al., (1988), "Anticarcinogenesis mechanisms, as evaluated in the multistage mouse skin model" *Mutation Research* 202:421–7 published in Netherlands.
Rotstein, et al., (1988), "Effect of exogenous glutathione on tumor progression in the murine skin multistage carcinogenesis model" *Carcinogenesis,* 9(9):1547–51 published in England.
Rotstein, et al., (1987), "A Possible Role for Free Radicals in Tumor Progression" *Anticarcinogenesis and Radiation Protection,* pp. 211–219 published in USA.
Slaga (1980), "Cancer: Etiology, Mechanisms, and Prevention—A Summary" In: *Carcinogenesis,* 5:Chapter 12, pp. 243–262 published in New York, designated in UTSC:156 IDS and 1449 as AQ.
Slaga (1983), "Overview of Chemical Carcinogenesis and Anticarcinogenesis" *Radioprotectors and Anticarcinogens,* pp. 437–448 published in USA.
Slaga et al., "Studies on the Mechanism of Action of Antitumor Promoting Agents: Suggestive Evidence for the Involvement of Free Radicals in Promotion" *Radioprotectors and Anticarcinogens,* pp. 471–485 published in USA.
Slaga (1983), "Multistage Skin Carcinogenesis and Specificity of Inhibitors" *Modulation and Mediation of Cancer by Vitamins,* pp. 10–23, designated in UTSC:156 IDS and 1449 as AP published in Switzerland.
Slaga (1983), "Tumor Promotion and Skin Carcinogenesis" In: *Mechanisms of Tumor Promotion,* vol. II, Chapter 10, pp. 189–196 published in USA, designated in UTSC:156 IDS and 1449 as AN.
Slaga, (1984), "Can Tumour Promotion be Effectively Inhibited?" *Models, Mechanisms and Etiology of Tumor Promotion,* 56:497–506 published in France, designated in UTSC:156 IDS and 1449 as AK.

(List continued on next page.)

Primary Examiner—Jyothsna Venkat
(74) Attorney, Agent, or Firm—Denise L. Mayfield (57) ABSTRACT

The present invention concerns a formulation of vitamins, minerals and other beneficial supplements which has been demonstrated to be cancer-protective. It is believed that the formulations of the present invention will also protect against cardiovascular disorders, extend longevity as well as to facilitate immunological integrity in humans. More specifically, the invention is directed to a formulation and methods of manufacturing and administering a formulation containing vitamins and minerals in association with antioxidants, fish oils, enzymes, and amino acids. The formulations of the present invention provide synergistic relationships which have not previously been reported. As a preferred embodiment, the formulations of the present invention are manufactured as a sustained-release tableted dietary supplement and are intended as daily supplements.

4 Claims, 3 Drawing Sheets-

OTHER PUBLICATIONS

Talbert et al., (1989), "Antioxidants–Free radical fighters that keep you healthy" In: *A Powerful Cancer Defense—Antioxidants*, pp. 1–24 publication location is unknown, designated in UTSC:156 IDS and 1449 as AO.

Cohen et al., "Anticarcinogenic Effects of 2,3,7,8–Tetrachlorodibenzo–p–doxin on Benzo(a)pyrene and 7, 12–Dimethylbenz(a)anthracene Tumor Initiation, and Its Relationship to DNA Binding" *Cancer Research*, 39, 4027–4033, Oct., 1979 published in USA.

Slaga et al., "The Effects of Antioxidants on Skin Tumor Initiation and Aryl Hydrocarbon Hydroxylase$_1$," *Cancer Research*, 37, 1631–1635, Jun. 1977 published in USA.

DiGiovanni et al., "Effects of 7,8–Benzoflavone on Skin Tumor–Initiating Activities of Various 7– and 12–Substituted Derivatives of 7,12–Dimenthylbenz[a]anthracene in Mice" *National Cancer Institute*, vol. 61, No. 1, Jul. 1978 published in USA.

Viaje et al., "Effects of Antiinflammatory Agents on Mouse Skin Tumor Promotion, Epiderman DNA Sythesis, Phorbol Ester–Induced Cellular Proliferation, and Production of Plasminogen Activator" *Cancer Research*, vol. 37, pp. 1530–1536, May 1977 published in USA.

Schwarz et al., "Fluocinolone Acetonide: A Potent Inhibitor of Mouse Skin Tumor Promotion and Epidermal DNA Synthesis," *Chem.–Biol. Interactions*, 17(1977) 331–347 published in Netherlands.

DiGiovanni et al., "Time–dependent Inhibition by 2,3,7,8–Tetrachlorodibenzo–p–dioxin of Skin Tumorigenesis with Polycyclic Hydrocarbons," *Cancer Research*, vol. 40, 1580–1587, May 1980 published in USA.

Slaga et al., "The Effects of Benzoflavones on Polycyclic Hydrocarbon Metabolism and Skin Tumor Initiation," *Chem.–Biol. Interactions*, vol. 17 (1977) 297–312 published in Netherlands.

Slaga, et al., "Strain Differences and Solvent Effects in Mouse Skin Carcinogenesis Experiments Using Carcinogens, Tumor Initiators and Promoters" *Progress in Experimental Tumor Research*, vol. 26, pp. 85–109, 1983 published in Switzerland.

Weeks et al., "αDifluoromethylornithine, an irreversible inhibitor of ornithine decaboxylase, inhibits tumor promoter–induced polyamine accumulation and carcinogenesis in mouse skin" *Proc. Natl. Acad. Sci.*, USA, vol. 79, pp. 6028–6032, Oct. 1982 published in USA.

Slaga et al., "Skin Tumor–Promoting Activity of Benzoyl Peroxide, a Widely Used Free Radical–Generating Compound" *Science*, vol. 213, pp. 1023–1025, Aug. 28, 1981 published in USA.

Slaga, T.J., "Cellular and Molecular Mechanisms Involved in Multistage Skin Carcinogenesis" *Skin Tumors Experimental and Clinical Aspects*, pp. 1–18, published in USA.

Aldaz, et al., "Progressive dysplasia and aneuploidy are hallmarks of mouse skin papillomas: Relevance to malignancy" *Proc. Natl. Acad. Sci. USA*, vol. 84, pp. 2029–2032, Apr. 1987 published in USA.

Aldaz, et al., "Sequential Trisomization of Chromosomes 6 and 7 in Mouse Skin Premalignant Lesions" *Molecular Carcinogenesis*, 2:22–26 (1989) published in USA.

Slaga, et al., "Critical Genetic Determinants and Molecular Events in Multistage Skin Carcinogenesis" *Symposium on Fundamental Cancer Research*, vol. 39, 1987 published in USA.

Slaga, et al., "Studies on the mechanism of skin tumor promotion: Evidence for several stages in promotion" *Proc. Natl. Acad. Sci.*, USA, vol. 77, No. 6 pp. 3659–3663, Jun. 1980 published in USA.

Nelson et al., "Effects of inhibitors of tumor promotion on 12–o–tetradecanoylphorbol–13–acetate–induced keratin modification in mouse epidermis" *Carcinogenesis*, vol. 3 No. 11 pp. 1311–1315, 1982 published in England.

Solanki, et al., "The reduction of tumor initiating activity and cell mediated mutagenicity of dimethylbenz[a]anthracene by a copper coordination compound" *Pharm. 18*, pp. 129–131, 1983 published in England.

Fischer et al., "Diazepam Inhibition of Phorbol Ester Tumor Promotion" *Cancer Letters*, vol. 19, 181–187, 1983, published in Ireland.

Slaga, T.J., "Multistage Skin Carcinogenesis: A Useful Model for the Study of the Chemoprevention of Cancer" *Acta Pharmacologica et Toxicologica*, vol. 55, Supl. 2, pp. 107–124, 1984 published in Denmark.

Slaga, T.J., "SENCAR Mouse Skin Tumorigenesis" in *Handbook of Carcinogen Testing*, pp. 230–250, 1985, published in USA.

Fischer, et al., "Effects of antihistamines on phorbol ester tumor promotion and vascular permeability changes" *Carcinogenesis*, pp. 991–996, 1990 published in England.

* cited by examiner

TIME RELEASE FORMULATION OF VITAMINS, MINERALS AND OTHER BENEFICIAL SUPPLEMENTS

This application is a continuation-in-part of U.S. Ser. No. 07/555,949 filed Jul. 19, 1990, now abandoned which is a divisional application of Ser. No. 07/475,641 filed Feb. 5, 1990 now abandoned, both of which are incorporated by reference herein.

The U.S. Government has rights to this invention pursuant to the following grants: NCI CA 34890 (Y01-CP-70227), NCI CA 34962 (CA20076), NCI CA 34521 and NCI CA 43278.

BACKGROUND OF THE INVENTION

Vitamins and minerals may be broadly defined as substances that are essential for the maintenance of normal metabolic function but are not synthesized in the body. These substances must be furnished from an exogenous source. A healthy individual ingesting a well-balanced diet receives adequate amounts of vitamins and minerals from food. Vitamins obtained in this manner are not generally regarded as drugs.

However, there are many situations in which the concentration of one or more vitamins or minerals in the body tissues may be suboptimal. When such circumstances arise or can be anticipated, it is the common practice to administer vitamins or minerals in a chemically pure form. When employed in this manner, vitamins and minerals may be regarded as drugs and a knowledge of their pharmacological properties is desirable. For example, large doses of various vitamins are frequently employed for the treatment of disorders that are not etiologically related to vitamin deficiency. The implication is that such large doses may exert pharmacodynamic actions that are useful in therapy. It should be noted, however, that excessive administration of certain vitamins, notably vitamin A, can cause untoward toxic effects.

In today's fast paced society many physicians and dieticians believe that a daily dietary vitamin and mineral supplement acts prophylactically to prevent pathologies associated with vitamin and mineral deficiencies. These supplements typically include several vitamins and minerals, and are referred to as multi-vitamin formulations. Examples of these preparations include One-A-Day® and Centrum® multi-vitamins. Researchers have suggested that multi-vitamins which include large quantities of vitamins and minerals are effective both for prophylactic purposes and for the treatment of an enormous variety of illnesses. Many millions of individuals living in the United States regularly ingest multi-vitamin preparations.

Some of these multi-vitamin preparations contain amounts of vitamins and minerals that are in excess of the RDA daily requirements. In the case of the water-soluble vitamins, there is little harm done to the body because of the low toxicity of this class of compounds. The low toxicity of the water-soluble vitamins is attributable to the fact that excess quantities of these substances are rapidly excreted in the urine. In the case of the lipid-soluble vitamins, the compounds accumulate in the body fat and can cause untoward toxic effects.

It is extremely important to distinguish between supplemental and therapeutic vitamin preparations. The latter contains much larger quantities of the individual vitamins and minerals than do the supplemental preparations. The present invention is directed to supplemental preparations.

The use of dietary multi-vitamin supplements should be considered by the physician in a wide variety of situations. Such situations may result from (1) inadequate vitamin intake, (2) mal-absorption syndromes, and (3) increased tissue requirements.

Vitamin deficiency due to an inadequate intake arises in a variety of circumstances. There are still large parts of the world and even considerable areas in the United States where, owing to poverty, the population eats a diet inadequate in terms of vitamin content. Moreover, there are areas where the prevalence in the diet of one particular type of food results in a relatively high incidence of vitamin deficiencies. Eccentric diets resulting from psychiatric disturbance, individual idiosyncrasies, religious beliefs, or food fads are other major causes of vitamin deficiency. A decrease in food consumption because of excess use of alcoholic beverages, poor appetite, dieting to combat obesity, or restricted diets prescribed by physicians for the management of specific diseases represents a further group of situations in which vitamin deficiency can arise.

A disturbance in absorption of vitamins is also seen in a variety of conditions. Examples are diseases of the liver and biliary tract, prolonged diarrhea from any cause, hyperthyroidism, pernicious anemia, and a variety of other disorders of the digestive system. Moreover, since a substantial proportion of certain vitamins is provided by the bacteria of the gastrointestinal tract, treatment with antimicrobials that alter the intestinal bacterial flora may lead inevitably to a decreased vitamin absorption.

Increased tissue requirements for vitamins also occur under a variety of conditions so that a nutritional deficiency may develop on a diet that had previously been adequate. Such situations can occur in both health and disease. In healthy individuals, for example, there is a greater requirement for various nutrients, including vitamins, during growth, during periods of hard physical work, exercise, during pregnancy, lactation, and menstruation. Diseases associated with an increased metabolism, such as hyperthyroidism, and conditions accompanied by fever or tissue wasting also increase the body's requirements for vitamins. There is also good evidence that vitamin requirements increase during stress and after injury.

Multiple-vitamin therapy, using supplemental dietary multi-vitamins, is desirable in a variety of situations. Since deficiency of a single vitamin is rarely encountered clinically, it is customary practice in cases of suspected vitamin deficiency, as well as in prophylactic treatment, to recommend that multiple-vitamin therapy be administered. Typical of the multi-vitamins available are One-A-Day and Centrum multi-vitamins. (Table 3). Multi-vitamins such as these provide a great number of the essential vitamins and minerals needed by healthy individuals. Further, these preparations include electrolytes, and trace elements.

Recently, it has been determined that antioxidants, and free radical scavenging agents are protective against the development of certain cancers. Although, multi-vitamin preparations currently available include many needed vitamins and minerals, they do not include the antioxidants and/or free radical scavengers which have been shown to enhance the immune system and to prevent certain cancers, cardiovascular disorders, inflammatory diseases and to slow aging. Further, currently available multi-vitamin preparations do not include cardio-protective inositol or polyunsaturated fatty acids having an eicosapentaenoic acid: docosahexenoic acid ratio of about 18:12 commonly referred to as Omega-3 fish oils. Still further, several enzymes, amino acids, and dietary supplements which are known to be necessary and beneficial in supplementing an individual's diet are not included in presently available multi-vitamin formulations. Accordingly, a new multi-vitamin dietary supplement is needed which incorporates many of these beneficial ingredients into a stable pharmaceutical preparation.

The U.S. Pat. No. 4,599,234 issued to Amer, Jul. 8, 1986, describes a diet comprising a source of selenium, butylated hydroxytoluene or butylated hydroxyanisole, and β-carotene that reduces the effect of carcinogens presented in the diet. The issued claims indicate a weight ratio of selenium:BHT:β-carotene of 1:0.5:0.05. In contrast, the optimal ratio of these ingredients in the formulation of the present invention is 1:2000:120. Taking into account the range of concentrations of these ingredients indicated in this invention, the closest ratio to that of Amer is 1:100:15.

The U.S. patent issued to Newmark (4,022,913) May 10, 1977 describes high potency compositions of vitamin A acetate and/or vitamin A alcohol stabilized against the formation of crystals by vitamin A palmitate. The compositions can contain antioxidants such as BHA, BHT propyl gallate, Vitamin E, and Vitamin C which are customarily utilized as a preservative in this type of preparation. Newmark does not teach that any of these antioxidants are cancer-protective.

The present invention concerns development of a multi-vitamin dietary supplement formulation which includes several dietary supplements which are cancer-protective. By including cancer- and cardio-protective immunostimulatory compounds in a multi-vitamin formulation, the present invention advantageously provides the general population the benefits of recent scientific research which has discovered that several agents are, for example, cancer- and cardio-protective. Accordingly, it is believed that the inventive methods and formulations will provide the general population with an improved multi-vitamin formulation capable of reducing the incidence of diseases such as cancer and heart disease while enhancing longevity and the immune system.

In still another aspect of the present invention, a method of inhibiting tumor-promoting effects of carcinogens in an animal is provided, the method comprising the administration of a daily dietary supplement at prophylactically effective levels including the formulation of the present invention.

Previous to the formulation of the present invention, no one had demonstrated the efficacy of these particular ingredients or the ratio of these particular ingredients of the present formulation in inhibiting the tumor-promoting effects of carcinogens in animals.

SUMMARY OF THE INVENTION

The present invention is directed to a formulation including vitamins, minerals and other beneficial supplements that is demonstrated to be cancer-protective. More specifically, the invention is directed to a formulation and methods of manufacturing and administering prophylactically effective amounts of a formulation containing vitamins and minerals in association with antioxidants, polyunsaturated fatty acids having an eicosapentaenoic acid:docosahexenoic acid ratio of about 18:12, food concentrate containing naturally occurring anti-oxidizing enzymes such as catalase and superoxide dismutase, for example, and amino acids. The formulations of the present invention exploit novel synergistic relationships which have not previously been reported in the inhibition of the induction of tumors, inhibition of spontaneous tumor formation and increase in lifespan.

One aspect of the present invention is directed to a daily multi-vitamin and mineral dietary supplement which comprises BHA or BHT, propyl gallate, Vitamin E, Vitamin C, β-carotene, and Selenium. Combinations of these ingredients are shown to inhibit tumor-promoting effects of carcinogens in an animal.

Several of the antioxidants, vitamins and minerals contained in the formulation have been shown to inhibit the induction of cancer at several stages in the multistage process. For example, B-carotene, glutathione, cysteine, BHA, BHT, Vitamins A, C and E, as well as selenium, inhibit the tumor initiation, promotion and progression stages of cancer. The heretofore unrecognized synergistic effects of BHA and Vitamin E, for example, may be related to the observations that BHA inhibits tumor promoter-induced polyamine synthesis, and that Vitamin E inhibits promoter-induced hyperplasia, thus leading to a synergistic effect. Furthermore, Vitamins A, C and E, selenium, BHA, BHT, and propyl gallate inhibit tumor initiation by counteracting the covalent binding of carcinogen to DNA and the mutagenic effect of carcinogens.

A further aspect of the present invention is directed to a multi-vitamin and mineral supplement including antioxidants in combination with certain preferred amino acids selected from the group consisting of reduced L-glutathione, L-cysteine, methionine, glutamine, and taurine. According to a preferred embodiment, the present inventive formulation further includes at least one of the following beneficial ingredients: polyunsaturated fatty acids having an eicosapentaenoic acid:docosahexenoic acid ratio of about 18:12, para-aminobenzoic acid, superoxide dismutase, catalase (these two enzymes being preferably obtained from a food concentrate), a citrus bioflavonoid, and inositol. Preferably, the reduced L-glutathione and the polyunsaturated fatty acids are microencapsulated in the present inventive formulation.

Preferably, the supplement of the present invention includes (but is not limited to) the following vitamins and minerals in an amount equal to or greater than the minimum daily requirement in man: folic acid, vitamin $B_1$, vitamin $B_2$, niacinamide, vitamin $B_6$, vitamin $B_{12}$, vitamin $D_3$, biotin, pantothenic acid, vitamin $K_1$, calcium, iodine, potassium, iron, magnesium, copper, zinc, manganese, chromium, molybdenum, vanadium, silicon, and boron.

An important aspect of the present invention is directed to a method of inhibiting tumor-promoting effects of carcinogens as well as increasing longevity and augmenting the immune system in an animal. The method includes the step of administering prophylactically effective amounts of (preferably daily) a dietary multi-vitamin and mineral supplement including antioxidants and other beneficial substances of the present invention at prophylactically effective levels. A prophylactically effective amount is an amount sufficient to inhibit said tumor promotion by carcinogens in an animal.

A still further aspect of the present invention is directed to the production of a sustained-release tableted dietary supplement which is intended to be administered one to three times daily.

DESCRIPTION OF THE PREFERRED EMBODIMENTS

The present invention concerns a formulation of vitamins, minerals and other beneficial supplements. It is demonstrated that the formulations of the present invention will protect against certain cancers. It is believed that the formulations will protect against cardiovascular disorders and immunological disorders in humans. Generally, the invention is directed to a formulation and methods of manufacturing and administering a formulation containing vitamins and minerals in association with antioxidants, polyunsaturated fatty acids having an eicosapentaenoic acid:docosahexenoic acid ratio of about 18:12, anti-oxidizing enzymes preferably contained in food concentrates, and amino acids. It is demonstrated that the formulation of the present invention is beneficial in treating or inhibiting the tumor-promoting effects of carcinogens. The formulation will also be beneficial in treating various vitamin deficiencies, cardiovascular disease and immunological disorders.

The formulations of the present invention exploit some synergistic relationships which have not previously been reported. The formulations of the present invention are particularly well adapted as a daily dietary supplement. The present invention further involves a method for administering the formulations of the present invention to a person in need thereof. The preparation of the present formulations is also a component of the present invention.

Explicit support for this continuation-in-part application is found throughout the parent application Ser. No. 07/555,949 as indicated by the abstract:

The present invention concerns a formulation of vitamins, minerals and other beneficial supplements. It is believed that the formulations of the present invention will not only extend longevity but also protect against diseases such as certain cancers and cardiovascular disorders as well as to facilitate immunological integrity in humans. More specifically, the invention is directed to a formulation and methods of manufacturing and administering a formulation containing vitamins and minerals in association with antioxidants, fish oils, enzymes, and amino acids. The formulations of the present invention provide synergistic relationships which have not previously been reported. As a preferred embodiment, the formulations of the present invention are manufactured as a sustained-release tableted dietary supplement and are intended as daily supplements.

Table 1 shows the anti-cancer effects of various components of the present formulation, individually and in synergistic combination.

TABLE 1

Effects of antioxidants on Skin Tumor Promotion[a]

| Antioxidant (mg) | Tumor Response (% Inhibition) |
|---|---|
| Control (DMBA + TPA) | 0 |
| BHA (0.5) | 35 |
| BHT (0.5) | 32 |
| Propyl gallate (0.5) | 40 |
| Vitamin E (0.1) | 25 |
| Vitamin C (0.5) | 30 |

TABLE 1-continued

Effects of antioxidants on Skin Tumor Promotion[a]

| Antioxidant (mg) | Tumor Response (% Inhibition) |
|---|---|
| B-carotene (0.5) | 20 |
| Selenium (0.004) | 23 |
| BHA (0.5) + BHT (0.5) | 92 |
| BHA (0.5) + Vit E (0.1) | 86 |
| BHA (0.5) + Vit C (0.5) | 98 |
| Vit E (0.1) + Selenium (0.004) | 94 |
| Vit E (0.1) + B-carotene (0.5) | 94 |
| BHA (0.5) + B-carotene (0.5) | 87 |
| BHT (0.5) + Vit E (0.1) | 89 |
| BHT (0.5) + Vit C (0.5) | 88 |
| BHT (0.5) + B-carotene (0.5) | 91 |
| Propyl gallate (0.5) + Vit E (0.1) | 78 |
| Propyl gallate (0.5) + Vit C (0.5) | 92 |
| Propyl gallate (0.5) + B-carotene (0.5) | 84 |
| BHA (0.1) + BHT (0.1) + Vit E (0.1) + B-carotene (0.1) | 97 |

[a]30 female mice (SENCAR) per group were used. The mice were initiated with 10 nmoles of 7,12-diethylbenzanthracene and promoted with 1 ug of TPA (12-0-tetradecanoylphorbol-13-acetate) 2 x/wk. The antioxidants were applied simultaneously with TPA for the duration of experiment (30 weeks).

Table 2 illustrates the effects of certain antioxidant components of the present formulation on all the known spontaneous tumor formations and longevity in mice.

TABLE 2

Effects of Antioxidants on Aging and Spontaneous Tumor Formation in Mice[a]

| Antioxidants[b] | Spontaneous Tumor Formation (% of Control) | Increase in Lifespan (%) |
|---|---|---|
| Normal Diet | 100 | — |
| BHA | 46 | 132 |
| BHT | 56 | 124 |
| Propyl gallate | 62 | 127 |
| BHT + propyl gallate | 38 | 136 |

[a]100 mice (SENCAR) (50 males and 50 females) were used for each group. The groups receiving the antioxidants had them introduced in the normal laboratory chow (Wayne Research Animal Diet) at 0.5%.

Table 3 illustrates the effects of antioxidant mixture in the diet on two-stage skin carcinogenesis.

TABLE 3

Effects of Antioxidant Mixture in the Diet on Two-Stage Skin Carcinogenesis[a]

| % of Diet | Tumor Response (% Inhibition) |
|---|---|
| Control Diet | 0 |
| 0.5% Antioxidant Mixture[b] | 28 |
| 1.0% Antioxidant Mixture[b] | 46 |
| 5.0% Antioxidant Mixture[b] | 72 |

[a]30 female mice (SENCAR) per group were used. All groups of mice were initiated with 10 nmols of 7,12-dimethylbenzanthracene and promoted with 1 μg of TPA (12-0-tetradecanoylphorbol-13-acetate) 2x/wk. The various diets were started one week before initiation and continued for the duration of the experiments.
[b]The antioxidant mixture in the diet contained the following: B-carotenes, vitamin A, vitamin E, vitamin $D_3$, calcium ascorbate, sodium selenate, zinc gluconate, copper gluconate, D,L-methionine, L-cysteine HCl, taurine, glutathione, BHA, BHT, propylgallate, sodium benzoate, citrus bioflavonoids, and vegetable cultures of SOD and catalase.

Core ingredients in the most preferred formulation of the present invention are the antioxidants and/or free radical scavenging agents of Table 1 which have a synergistic effect on the inhibition of tumor promotion. The following are the Core ingredients:

Propyl gallate
Vitamin E
Vitamin C
BHA or BHT
B-carotene
Selenium

The significance and content of the Core ingredients may be described as follows:

In one important aspect of the present invention, the formulation includes at least one antioxidant. The antioxidant is preferably selected from the group consisting of butylated hydroxyanisole, butylated hydroxytoluene and propyl gallate. The inventive formulation may include one, or, more preferably, several of the preferred antioxidants in combination. According to one embodiment, the inventive formulation includes butylated hydroxyanisole (BHA) or butylated hydroxytoluene (BHT), and propyl gallate. BHA, BHT and propyl gallate are all antioxidants used to stabilize cosmetic, pharmaceutical, and food products. It has been reported that these agents protect normal cells against radiation, free radicals, toxic chemicals and chemical carcinogens. It has been demonstrated in Table 1 that these agents are protective against the promotion of cancer by cancer-causing agents in SENCAR mice. In addition, it has been demonstrated in Table 1 that these agents increase longevity in SENCAR mice. The SENCAR mouse is a valid testing system for the ability of a compound to inhibit tumor initiation and promotion. A good dose-response relationship exists for 7, 12-dimethylbenzanthracene to initiate skin tumors in these mice and they are sensitive to TPA (12-0-tetradecanoylphorbol-13-acetate) promotion [Slaga(1983) "Multistage Skin Carcinogenesis and Specificity of Inhibitors" in: Modulation and Mediation of Cancer by Vitamins, pp. 10–23.]. Further, the preferred antioxidants of the present invention have been reported to protect against cardiovascular disorders, enhance immune function and increase longevity. The preferred antioxidants of the present invention work synergistically with several vitamins, minerals, amino acids, enzymes, and other antioxidants or free radical scavengers included in the formulation of the present invention as will be described in detail below.

According to one embodiment, BHA is included in a daily dietary multi-vitamin and mineral formulation for humans administered on a 1–3 times daily basis. Preferably, from about 1 to amount 300 mg of BHA is included in combination with a number of vitamins and minerals. More preferably, however, the formulation includes from about 10 to about 150 mg of BHA, and most preferably, about 50 mg of BHA. BHA may be included in the inventive formulation as butylated hydroxyanisole, 3-tert-butyl-4-hydroxyanisole, or 2-tert-butyl-4-hydroxyanisole, but most preferably is butylated hydroxyanisole.

According to another preferred embodiment, BHT is included in a daily dietary multi-vitamin and mineral formulation. Preferably, from about 1 to amount 300 mg of BHT is included in combination with a number of vitamins and minerals. More preferably, however, the formulation includes from about 10 to about 150 mg of BHT, and most preferably, about 50 mg of BHT.

According to further embodiment, propyl gallate is included in the daily dietary multi-vitamin and mineral formulation. Preferably, from about 1 to amount 300 mg of propyl gallate is included in combination with a number of vitamins and minerals. More preferably, however, the formulation includes from about 10 to about 150 mg of propyl gallate, and most preferably, about 50 mg of propyl gallate.

Vitamin E is a fat soluble vitamin which functions as an antioxidant protecting lipid membranes against oxidation. Deficiencies in vitamin E can increase the tendency of blood to clot. Vitamin E works synergistically with several vitamins, minerals, e.g., selenium, and antioxidants to lower cancer rates and to increase longevity. The dosage of vitamin E included is preferably from about 10 to 100 units as DL-alpha tocopherol acetate, DL-alpha tocopherol succinate, water soluble DL-alpha tocopherol acetate or succinate, emulsified DL-alpha tocopherol acetate, D-alpha tocopherol acetate, D-alpha tocopherol succinate, mixed tocopherols, emulsified D-alpha tocopherol acetate, emulsified mixed D-tocopherols, water soluble D-alpha tocopherol acetate, water soluble mixed D-tocopherols, D-alpha tocopherol, emulsified D-alpha tocopherol, water soluble D-alpha tocopherol, or alpha tocopherol nicotinate. Most preferably, however, the dosage of vitamin E is about 100 units as vitamin E, DL-alpha tocopherol acetate.

Vitamin C is a water soluble essential vitamin. It is critical in producing and maintaining collagen, promotes healing of wounds, aids tooth and bone formation, and is important in producing hormones that regulate basal metabolic rate and body temperature. Vitamin C also acts as an antioxidant and may counteract nitrosamines formed in the intestinal tract, and, therefore, helps reduce the rates of certain kinds of cancers. Vitamin C works synergistically with several other vitamins, as well as minerals and antioxidants, to lower cancer rates and to increase longevity. The dosage of vitamin C included is preferably from about 10 to 1,000 mg as ascorbic acid, or salts of ascorbic acid including calcium ascorbate, magnesium ascorbate, sodium ascorbate, potassium ascorbate, esterified ascorbic acid, ascorbyl palmitate. Most preferably, however, the dosage of vitamin C is about 250 mg as calcium ascorbate.

Beta carotene or, provitamin A is a precursor to vitamin A. Beta carotene must be converted by the body into active retinol-type vitamin A to be utilized. Beta carotene is also a potent antioxidant and may prevent certain types of cancer. Beta carotene works synergistically with several vitamins, minerals and antioxidants to lower cancer rates and to increase longevity. Although Vitamin A and other retinoids have been shown to inhibit the induction of skin cancer in mice, an unexpected result has been the lack of an inhibitory activity by β-carotene in the mouse skin carcinogenesis system. However, if β-carotene is given with low doses of vitamin E, BHA or BHT, it very effectively enhances their activity in a synergistic manner. The dosage of beta carotene included is preferably from about 2,500 to 7,500 provitamin A units as water soluble beta carotene, or emulsified beta carotene, and most preferably 5,000 provitamin A units as emulsified beta carotene.

Selenium works synergistically with vitamins to inhibit the promotion of skin tumors as shown in Table 1. Selenium also helps maintain proper immune system function. It is an essential component of glutathione peroxidase, and as an antioxidant helps protect cells from free radical damage and toxic effects of certain chemicals. Deficiencies are linked with increased risk of various cancers, along with increased risk of stroke, angina and heart attack. Preferably, the dosage of selenium included is from about 2 mcg to about 100 mcg as sodium selenate, selenous acid, potassium selenate, selenium oxide, selenomethionine, selenium yeast, selenium vegetable culture, selenium amino acid chelate, selenium proteinate, selenium ascorbate, selenium aspartate, sodium selenite, sodium selenate, potassium selenite, selenocystine, magnesium potassium selenate, magnesium selenate, cupric selenate, cupric selenite, zinc selenate, zinc selenite, calcium selenate, calcium selenite, selenium picolinate, selenium glycinate, and selenium glycerophosphate. Most preferably, however, the dosage of selenium is about 25 mcg as sodium selenate.

The core ingredients can also interact synergistically with the following components, vitamins and minerals which additionally are included in the preferred formulation (Core II):

Vitamin A
Copper
Zinc
Manganese
inositol
PABA
bioflavonoids
reduced L-glutathione
N-acetyl-L-Cysteine
Potassium sorbate or sorbic acid
Sodium benzoate
Taurine
D L-Methionine
L-glutamine
SOD
Catalase and Polyunsaturated fatty acids having an eicosapentaenoic acid:docosahexenoic acid ratio of about 18:12.

Due to their importance especially in the prevention of cardiovascular disorders, polyunsaturated fatty acids having an eicosapentaenoic acid:docosahexenoic acid ratio of about 18:12, PABA and inositol are an important part of the Core II formulation.

The Core II ingredients may be described as follows:

Vitamin A is a fat soluble vitamin essential in cell differentiation, vision, immunity, healthy skin, hair, and mucous membranes. This vitamin is also necessary for proper reproduction, bone growth and development of teeth. Deficiencies have been associated with a higher incidence of certain cancers. Vitamin A appears to work synergistically with several other vitamins, as well as minerals and antioxidants, to lower cancer rates and to increase longevity. The dose of vitamin A preferably included is from about 1,000 to 3,000 i.u., and more preferably, about 2,000 i.u. Preferably, the vitamin A source included in the formulation is vitamin A acetate, vitamin A palmitate, retinol, and retinal. The source of vitamin A may be water soluble, fat soluble, or emulsified. Most preferably, however, the vitamin A source is emulsified vitamin A acetate.

Copper is a trace mineral essential for the formation of red blood cells and the utilization of iron. It also functions in electron transport, connective tissue metabolism and the development of the nervous system. Deficiencies have been linked to nervous system disorders, bone disorders (spontaneous fractures) and anemia. Copper may protect against certain types of cancers. Copper dosage is 0.2 to 20 mg as copper oxide, cupric acetate, cupric butyrate, cupric subcarbonate, cupric chloride, cupric citrate, cupric formate, cupric gluconate, cupric glycinate, cupric hydroxide, cupric oxide, cupric stearate, cupric sulfate, cupric subsulfate, copper gluconate, copper amino acid chelate, copper salicylate, copper proteinate, cupric tyrosinate, copper glycerophosphate, and copper picolinate.

Zinc is a trace mineral essential to cell multiplication, tissue regeneration and wound healing, sexual maturity, and proper growth. Zinc is required for many enzymatic functions throughout the body, and also helps regulate the immune system and insulin metabolism. Preferably, the dosage of zinc included is from about dosage 2 to about 30 mg as zinc oxide, zinc acetate, zinc benzoate, zinc caprylate, zinc carbonate, zinc chloride, zinc citrate, zinc formate, zinc lactate, zinc selenate, zinc stearate, zinc sulfate, zinc picolinate, zinc gluconate, zinc sulfate heptahydrate, zinc sulfate monohydrate, zinc succinate, zinc amino acid chelate, zinc proteinate, zinc fumarate, zinc aspartate, zinc ascorbate, and zinc glycerophosphate. Most preferably, however, the dosage of zinc is about 15 mg as zinc oxide.

Manganese is a trace mineral essential to enzyme systems involved in bone development, insulin production as well as other enzyme systems. It is also required for the synthesis of cartilage mucopolysaccharides. Preferably, the manganese dosage is from about 0.5 to about 5 mg as manganese gluconate, manganese acetate, manganese carbonate, manganese chloride, manganese dioxide, manganese hypophosphite, manganese iodide, manganese silicate, manganese sulfate, manganese picolinate, manganese glycerophosphate, manganese lactate, manganese amino acid chelate, manganese proteinate, manganese ascorbate, manganese aspartate, manganese citrate, manganese fumarate, and manganese glycinate. More preferably, the manganese dosage is about 2.5 mg as manganese gluconate.

Polyunsaturated fatty acids having an eicosapentaenoic acid:docosahexenoic acid ratio of about 18:12 are omega-3 (EPA/DHA) fish oils. Increased dietary levels of polyunsaturated fatty acids reduces platelet aggregation and has been linked to a lower incidence of heart disease and cancer. omega 3 fish oils, preferably having an EPA:DHA ratio of about 18:12, are included in the supplement of the present invention in a dosage of from about 10 to about 1,000 mg, more preferably, however, the dosage is from about 50 to about 800 mg, and most preferably about 200 mg. The omega-3 fish oil is preferably included as microencapsulated omega-3 fish oils, Omega 3 fish oils, cod liver oil, salmon oil, microencapsulated salmon oil, emulsified cod liver oil, emulsified salmon oil, eicosapentaenoic acid, docosahexenoic acid, emulsified eicosapentaenopic acid, emulsified docosahexaenoic acid, fish oil, EPA, max EPA sardine oil, microencapsulated sardine oil, halibut oil, or microencapsulated halibut oil. Most preferably, however, the omega-3 fish oil is microencapsulated omega-3 fish oil.

Inositol plays a vital metabolic role at the cellular level. Inositol is a lipotropic agent and plays a role in membrane and lipoprotein function. Inositol is preferably included in a dosage of from 5 to about 100 mg, and most preferably, about 50 mg.

According to one embodiment, the daily dietary multivitamin and mineral supplement of the present invention further includes para-aminobenzoic acid (PABA) in combination with the preferred amino acids and antioxidants of the present invention. PABA is an essential coenzyme in the metabolism of proteins and in the formation of red blood cells. PABA works synergistically with pantothenic acid. It has been reported that PABA may provide some protection against hypertension and certain cancers. PABA is preferably included in the formulations of the present invention as para-aminobenzoic acid, potassium para-aminobenzoate, sodium para-aminobenzoate, magnesium para-aminobenzoate, calcium para-aminobenzoate. Most preferably, however, PABA is included as the acid in a dosage of from about 10 to about 100 mg, and most preferably, about 40 mg.

Bioflavonoids are biologically active compounds that have been shown to act as antioxidants, protecting vitamin C and other components from oxidation. Certain bioflavonoids have been shown to have a protective effect against some cancers. The dosage of the bioflavonoid included is from about 2 to 200 mg, more preferably, from about 25 to about 150 mg, and most preferably, about 50 mg. Preferable sources of bioflavonoid include citrus bioflavonoid, vitamin P, vitamin P complex, rutin, orange peel bioflavonoid, grapefruit peel bioflavonoid, lemon bioflavonoid, lime bioflavonoid, flavonoids, kaempferol, narigenin, apigenin, naringin, naringenis, myricetin, delphinidin, quercetin, phloretin, cyanic, catechin, morin, phloridzin, phloretin, 3-hydroxyflavones, 3-deoxyflavonols, isorhamnetin, luteolin, tricin, chrysoeriol, hesperitin, eriodictyon, techtrochrysin, silybin, taxifolin, pinocembrim, galangin, robinin, diosmetin, kaempferide, fisetin, rhamnetin, and 3-0-methyl catechin. The most preferable source is, however, citrus bioflavonoid.

It is believed that glutathione may protect normal cells against radiation, free radicals and other toxic materials, and certain cancers. Functionally, glutathione is the proton donor used by glutathione peroxidase to remove free radicals. Forms of glutathione useful in the practice of the present invention include: L-glutathione, S-ethylglutathione, S-butylglutathione, S-decylglutathione, S-heptylglutathione, S-methylglutathione, S-propylglutathione, S-pentylglutathione, S-octylglutathione and S-nonylglutathione. However, most preferably, glutathione is included in the formulations of the present invention as reduced L-glutathione in microencapsulated form. The dosage of glutathione included to the inventive formulation is preferably from about 1 to about 20 mg, and most preferably, about 10 mg.

L-Cysteine is an amino acid which has antioxidant properties and plays an important role in glutathione peroxidase activity. Cysteine also appears to have certain anticancer activity. Preferably, cysteine is included in the present invention as L-cysteine HCl, L-cysteine, L-acetyl cysteine, N-acetyl-L-cysteine, L-cysteine ethylester monohydrochloride, DL-cysteine, DL-cysteine HCl, L-cysteine methylester. However, it is most preferred, that cysteine is included as N-acetyl-L-cysteine HCl, in a dosage of from about 5 to about 100 mg, and more preferably, about 50 mg.

Potassium sorbate or sorbic acid is useful as a mold and yeast prohibitor. Sorbic acid has been shown to increase the effectiveness of antioxidant mixtures by acting synergistically with them. The sorbic acid dosage is preferably from about 10 to 500 mg as potassium sorbate, sorbic acid, or sodium sorbate. Most preferably, however, the dosage of sorbic acid is about 200 mg as potassium sorbate.

Sodium benzoate, an antioxidant used to stabilize food and pharmaceutical products, according to another embodiment, is included in a daily dietary multi-vitamin and mineral formulation. Preferably, from about 1 to amount 300 mg of sodium benzoate is included in combination with a number of vitamins and minerals. More preferably, however, the formulation includes from about 1 to about 150 mg of sodium benzoate, and most preferably, about 4 mg of sodium benzoate. As described above, one embodiment of the inventive formulation includes sodium benzoate. However, it has been determined that potassium benzoate, benzoic acid, calcium benzoate, cuprous benzoate, cupric benzoate, manganese benzoate, nickel benzoate, magnesium benzoate are all also useful in the practice of the present invention.

Taurine is an amino acid used by the liver for conjugation with bile acids. It has also been suggested that taurine strengthens and stabilizes cellular membranes. High concentrations of taurine are found in the brain. Taurine, it is believed, acts in concert with the preferred antioxidants of the present invention to provide increased protection against cancer and certain cardiovascular diseases. Preferably, taurine is included in the formulations of the present invention in a dosage of from about 1 to about 20 mg, and most preferably, about 10 mg.

Methionine is an essential amino acid which has antioxidant properties. Methionine is the principal source of methyl groups which are, in turn, transferred to many diverse acceptors in important physiological reactions, such as, methyl transferases. Methionine is preferably include in the formulations of the present invention as DL-methionine, L-methionine, S-adenosylmethionine, N-acetyl-methionine, S-methyl-DL-methionine-sulfonium chloride. However, more preferably, methionine is included as DL-methionine, in a dosage of from about 1 to about 20 mg, and most preferably, about 10 mg.

Glutamine is an amino acid which serves as an amino donor in many reactions. Glutamine is critical for the de novo synthesis of purine and pyrimidine nucleotides. These nucleotides are critical to normal cell function and replication. Preferably, glutamine is included in the formulations of the present invention as L-glutamine, DL-glutamine, or N-acetyl-L-glutamine. However, most preferably, glutamine is included as L-glutamine, in a dosage of from about 1 to about 20 mg, and most preferably, about 10 mg.

Superoxide dismutase (SOD) stabilizes the formulations of the present invention and is an antioxidant. SOD prevents the formation of singlet oxygen, hydroxyl radicals and other reactive oxygen species. It is believed that SOD can protect against cancer, cardiovascular disorders and increase longevity. The dosage included of SOD (superoxide dismutase) is preferably from about 20 to about 500 units, more preferably, from about 100 to about 300, and most preferably about 150 units (i.u.) (McCord/Fridovich units). Preferable sources of SOD for the formulation of the present invention include purified liver SOD, bovine SOD, intercellular SOD, bovine liver SOD, erthrocytic SOD, extracellular SOD/, vegetable culture SOD, vegetable SOD, bovine lyophilized liver SOD, fractionated liver SOD, fractionated erythrocyte SOD, and bacterial SOD. The most preferable source of SOD is, however, vegetable SOD, particularly as a food concentrate.

Catalase also stabilizes the formulations of the present invention and compliments SOD. Catalase converts hydrogen peroxide into water and oxygen. It is believed that catalase protects against diseases such as cancer and cardiovascular disorders as well as increasing longevity. The dosage of catalase included is from about 5 mg to 500 units, more preferably, from about 100 to about 300 units, and most preferably, about 150 units (i.u.) (Baker Units). Preferable sources of catalase include that purified from bovine liver, fractionated liver, bacteria, Aspergillus niger, and vegetables. The most preferable source is, nm however, vegetables, particularly as a food concentrate.

Scientists have indicated that fragments of SOD and catalase retain catalytic activity. Initial experiments demonstrate that feeding SOD and catalase to animals as 2% of the diet decreases inflammatory hyperplasia caused by the application of tumor promoters on skin. These data are consistent with the indication that the enzymes or active fragments thereof are passing into the system to a significant degree.

Also, the following vitamins and minerals (Core III), although not unique, are necessary and important in this formulation because of their role in normal growth and general bodily needs. Once vitamins have crossed the intestinal walls, many function as co-enzymes essential to all cells. Because they work synergistically, or as a team, it is better to administer them together. A similar synergism is known for many of the minerals. They are as follows:

Folic Acid
Vitamin $B_1$
Vitamin $B_2$
Niacinamide
Vitamin $B_6$
Vitamin $B_{12}$
Vitamin $D_3$
Biotin
Ca Pantothenate
Vitamin $K_1$
Calcium
Iodine
Potassium
Iron
Magnesium
Chromium
Molybdenum
Vanadium
Silicon
Boron Compositions of the Core III formulations may be described as follows.

Folic Acid is an essential water-soluble vitamin. It is necessary for the synthesis of RNA and DNA, and therefore, vital in cell growth and division. Folic acid is important in red blood cell maturation and in other metabolic processes. The dose of folic acid included is from about 40 to about 1,2000 mcg as folic acid, and most preferably, about 400 mcg.

Vitamin $B_1$ (thiamine) is an essential water-soluble vitamin. It is important in the metabolism of carbohydrates and critical for the transmission of high-frequency impulses in the central nervous system as well as maintaining the integrity of the central nervous system. Preferably, the dosage of vitamin $B_1$ included is from about 1 to about 2 mg as thiamine hydrochloride, thiamine mononitrate, thiamine chloride naphthalene-1, 5-disulfonic acid salt, thiamine triphosphoriate salt, thiamine triphosphate ester, thiamine phosphoric acid ester phosphate salt, thiamine phosphoric acid ester chloride, and thiamine disulfide. Most preferably, however, the dosage of vitamin $B_1$ is about 1.50 mg as thiamine hydrochloride.

Vitamin $B_2$ (riboflavin) is an essential water-soluble vitamin which is required for the repair and growth of tissues as well as DNA synthesis. Vitamin $B_2$ assists in metabolizing nutrients, e.g., proteins, fats and carbohydrates, and therefore, is critical in the release of energy. Preferably, the dosage of vitamin $B_2$ is from about from 170 mcg to about 2 mg as riboflavin, riboflavin tetrabutyrate, riboflavin 5' phosphate sodium, and riboflavin monodiethanolamine salt dihydrate. Most preferably, however, the dosage of vitamin $B_2$ is about 1.75 mg as riboflavin.

Niacinamide is critical in the production of energy. Niacinamide is water-soluble, and is an essential constituent of coenzymes I and II that occur in a wide variety of enzyme systems involved in the anaerobic oxidation of carbohydrates. Niacinamide is necessary for DNA formation, and important for the integrity of the central nervous system. Preferably, the dosage of niacinamide included is from about 10 to about 30 mg as niacinamide, and most preferably, about 20 mg.

Vitamin $B_6$ is a term commonly used for a group of three vitamins: pyridoxine, pyridoxal and pyridoxamine. They are important in protein and amino acid metabolism and help to regulate blood glucose levels. These vitamins are needed to synthesize hemoglobin and are important in the proper function of the central nervous system. The dosage of vitamin $B_6$ is preferably from about 200 mcg to about 3 mg as pyridoxine hydrochloride, pyridoxal 5-phosphate, calcium pyridoxine 5-phosphate, pyridoxal. Most preferably, however, the dosage of vitamin $B_6$ is about 2 mg.

Vitamin $B_{12}$ is an essential water soluble vitamin. It is critical for bone growth, the integrity of the central nerve tissue, normal blood formation, and cell replication and DNA synthesis. Vitamin $B_{12}$ deficiencies are related to certain anemias. Vitamin $B_{12}$ is useful especially in the prevention of pernicious anemia. Preferably the dosage of Vitamin $B_{12}$ included is from about 2 to about 1000 mcg as cyanocobalamin, cobalamin, Co-methylcyanocobalamin, zinc-vitamin $B_{12}$-tannate, resin bound vitamin $B_{12}$, and coenzyme $B_{12}$.

Vitamin $D_3$ is an oil-soluble vitamin. Vitamin $D_3$ aids both the absorption of calcium and phosphorus. The primary role of vitamin $D_3$ is the mineralization of bones and teeth and the regulation of blood calcium levels. Vitamin $D_3$ is critical for the growth and differentiation of several tissues, and, it is believed, reduces the rate of certain cancers. The dosage of vitamin $D_3$ included is preferably from about 40 to about 4,000 units as vitamin $D_3$, water dispersable vitamin $D_3$, water-soluble vitamin $D_3$, and emulsified vitamin $D_3$. Most preferably, however, the dose of vitamin $D_3$ is about 600 units.

Biotin is a water-soluble vitamin essential in metabolism. It is a coenzyme in the synthesis of fatty acids and amino acids. The dosage of biotin is preferably from 10 to 100 mcg as biotin, and most preferably, about 30 mcg.

Calcium pantothenate is a source of pantothenic acid, a water-soluble vitamin. Pantothenic acid is involved with the metabolism of proteins, fats and carbohydrates in the form of exoenzyme A, and is involved in the synthesis of sterols, hormones, porphyrins and acetylcholine. The dosage of calcium pantothenate is preferably from about 1 to about 50 mg, and most preferably, about 10 mg.

Vitamin $K_1$ is an oil soluble vitamin which is necessary for the formation of prothrombinogen and other blood clotting factors. However, vitamin K-dependent protein in bone suggests a more complex role. Preferably, the dosage of Vitamin $K_1$ is from about 3 to 100 mcg as trans isomer of vitamin $K_1$, cis-trans isomers of vitamin $K_1$, emulsified trans isomer of vitamin $K_1$, emulsified cis-trans isomers of vitamin $K_1$, water soluble trans vitamin $K_1$, water soluble cis-trans isomer of vitamin $K_1$, vitamin $K_1$ oxide, trans vitamin $K_1$ oxide, emulsified cis-trans vitamin $K_1$ oxide, water soluble trans vitamin $K_1$, water soluble cis-trans vitamin $K_1$ oxide, vitamin $K_2$ (2-methyl -3- all trans-polyprenyl-1, 4 napthoquinone) and those compounds of vitamin $K_2$ which may possess side chains varying in length from $C_5$ (n=1) to $C_{65}$ (n=13), water soluble vitamin $K_2$ and water soluble compounds of compounds of $K_2$ which may possess side chains varying in length from $C_5$ (n=1) to $C_{65}$ (n=13), vitamin $K_5$, dihydrovitamin $K_1$, diphosphate ($0^1$, O⁴-diphosphoric acid) disodium salt of dihydrovitamin $K_1$, tetrasodium salt of dihydrovitamin $K_1$, tetrapotassium salt of dihydrovitamin $K_1$, diphosphate (O¹, O⁴-diphosphoric acid) dipotassium salt of dihydrovitamin $K_1$, vitamin $K_6$, vitamin $K_7$, vitamin $K_7$ hydrochloride, vitamin $K_5$ (II), emulsified vitamin $K_5$ (II), water soluble vitamin $K_5$ (II). Most preferably, however, the dose of vitamin $K_1$ is about 25 mcg.

Calcium is involved with the transmission of nerve impulses, muscle contraction and relaxation, blood clotting, structure and function of cell membranes and $B_{12}$ absorption. Dietary deficiencies are common and have been associated with accelerated bone loss resulting in alveolar bone loss and accompanying oral health problems, osteoporosis and hypertension. Calcium may also protect against certain type of cancer such as colon cancer. Preferably, the calcium dosage included is from about 40 to about 1,000 mg as dicalcium phosphate dihydrate, dicalcium phosphate, monobasic calcium phosphate, tricalcium phosphate, calcium carbonate, calcium chloride, calcium citrate, calcium fluoride, calcium gluconate, calcium glycerophosphate, calcium hydroxide, calcium lactate, calcium levulinate, calcium sulfate, calcium succinate, calcium ascorbate, calcium fumarate, calcium lysinate, calcium malate, calcium aspartate, calcium amino acid chelate, calcium caseinate, calcium proteinate, calcium picolinate, calcium aspartate, calcium alpha ketoglutarate, calcium caseinate, calcium hydroxide, bone meal, oyster shell, calcium glycerophosphate, calcium hypophosphite, calcium ferrous citrate, calcium formate, calcium hypochlorite, calcium methionate, calcium biphosphate, calcium stearate, calcium tartrate, hydroxyapatite, dolomite, calcium sulfate dihydrate, calcium sulfate hemihydrate, dicalcium phosphate dihydrate, calcium acetate, calcium pyrophosphate, calcium glycinate. More preferable sources of calcium include calcium citrate, calcium carbonate, which act as free radical scavengers, calcium pantothenate, and dicalcium phosphate dihydrate. Dicalcium phosphate dihydrate is source of calcium and phosphorus which functions in almost all aspects of metabolism, and also aids in the manufacturing (tableting) process.

Iodine is essential for proper thyroid functioning, and therefore, the regulation of the basal metabolic rate. The dosage of iodine included is from about 5 to 500 mcg as potassium iodide, sodium iodide, iodinated glycerol, kelp, Atlantic kelp, Pacific kelp, iodine-resublimed, potassium iodate, ferrous iodide, magnesium iodide, manganese iodide, iodine picolinate, iodine aspartate, iodine glycerophosphate. Most preferably, however, the dosage is about 150 mcg as potassium iodide.

Potassium is a major intracellular electrolyte. Potassium aids in the transmission of nerve impulses, the release of insulin, and the proper functioning of digestive enzymes. Potassium works with sodium to maintain the balance of body fluids. Preferably, the dosage of 10 to about 1000 mg potassium is from potassium chloride, potassium acetate, potassium bicarbonate, potassium carbonate, potassium citrate, potassium gluconate, potassium glycerophosphate, potassium hydroxide, potassium nitrate, dipotassium phosphate, potassium dihydrogen phosphate, tripotassium phosphate, potassium sorbate, potassium sulfate, potassium proteinate, potassium amino acid chelate, potassium fumarate, potassium alpha ketoglutarate, potassium malate, potassium ascorbate, potassium succinate, potassium aspartate, potassium/magnesium aspartate, or potassium picolinate.

Iron is an essential mineral and is needed to transport oxygen to the tissues throughout the body via hemoglobin and myoglobin. Iron is involved in the catalysis of many oxidative reactions within cells and is necessary for the proper functioning of many biochemical reactions. Iron plays a role in final steps of energy metabolism. Iron deficiencies are widespread, especially among women and children. Preferably, the dosage of iron included is from about 2 to about 50 mg as ferrous fumarate, ferrous carbonate mass, ferrous carbonate saccharated, ferrous chloride, ferrous citrate, ferrous gluconate, ferrous iodide, ferrous lactate, ferrous oxide, ferrous succinate, ferrous sulfate, ferrous ascorbate, iron amino acid chelate, ferrous aspartate, ferrous peptonate, iron proteinate, iron chloride, iron reduced, iron oxide saccharated, ferric glycerophosphate, and iron picolinate. Most preferred, however, the dosage of iron is about 18 mg as iron gluconate.

Magnesium is a mineral essential for every biological process including glucose metabolism, protein and nucleic acid synthesis, electrical balance of cells, and the transmission of nerve impulses. Magnesium effects the function and structure integrity and contractions of the heart and all other muscles. Dietary deficiencies are widespread. Deficiencies have been linked to cardiovascular diseases. Preferably, the dosage of magnesium included is from about 10 to about 500 mg as magnesium oxide, magnesium benzoate, magnesium carbonate hydroxide, magnesium chloride magnesium citrate, di-basic magnesium citrate, magnesium formate, magnesium hydroxide, magnesium iodide, magnesium lactate, magnesium peroxide, magnesium hydrogenphosphate, trimagnesium phosphate, magnesium silicate, magnesium stearate, magnesium sulfate, magnesium carbonate, magnesium gluconate, magnesium glycerophosphate, magnesium trisilicate, magnesium nicotinate, magnesium malate, magnesium amino acid chelate, magnesium picolinate, magnesium proteinate, magnesium lysinate, magnesium alpha ketoglutarate, and magnesium phosphinate hexahydrate. Most preferably, however, the dosage of magnesium is about 100 mg as magnesium oxide.

Chromium is a cofactor for insulin. Chromium is involved in carbohydrate metabolism, especially the utilization of glucose. Low chromium has been linked to diabetes and hypoglycemia. Low chromium has also been associated with heart disease. Chromium deficiencies are widespread. Preferably, the dosage of chromium included is from about 2 to about 50 mcg as chromium (+3) chloride, chromic acetate, chromic carbonate, chromic formate, chromic hydroxide, chromic nitrate, chromic oxide, chromic phosphate, chromic potassium sulfate, chromic sulfate, chromic picolinate, chromium polynicotinate, chromium soured yeast, chromium vegetable culture, chromium amino acid chelated, chromium proteinate, chromium aspartate, chromium ascorbate, chromium GTF yeast, chromium glycinate, and chromium glycerophosphate. Most preferably, the dosage of chromium is about 25 mcg as chromium (+3) chloride.

Molybdenum is considered to be an essential trace mineral. Molybdenum plays a role in iron metabolism. Preferably, the dosage of molybdenum included is from about 2 mcg to 100 mcg as sodium molybdate, molybdenum amino acid chelate, molybdenum ascorbate, molybdenum yeast, molybdenum vegetable culture, molybdenum disulfide, molybdenum sesquioxide, molybdenum trioxide, sodium phosphomolybdate, molybdenum picolinate, molybdenum glycinate, and molybdenum glycerophosphate. Most preferably, however, the dosage of molybdenum is about 25 mcg as sodium molybdate.

Vanadium is a trace mineral found in the diet. Possible biochemical and physiological functions for vanadium have been suggested as including lipid metabolism, glucose metabolism, bone, and tooth metabolism. Vanadium may serve a catalytic function or may be an enzyme cofactor. Preferably, the dosage of vanadium included is from about 2 mcg to about 100 mcg as sodium metavanadate, vanadium aspartate, vanadium amino acid chelate, vanadium proteinate, vanadium yeast, vanadium vegetable culture, potassium metavanadate, calcium vanadate, magnesium vanadate, ammonium metavanadate, vanadyl sulfate, oxytartarovanadate, vanadium picolinate, vanadium glycinate, and vanadium glycerophosphate.

Silicon functions as a biologic cross-linking agent that contributes to the structure and resilience of connective tissues, collagen, elastin and mucopolysaccharide. Silicon may be required for bone and cartilage collagen biosynthesis and is apparently involved in bone calcification. Preferably, the dosage of silicon included is from about 2 mcg to about 50 mcg as sodium metasilicate, silica amino acid chelate, silicon proteinate, silicon plant source, silicon vegetable culture, silicon source trachea, silicon source tendon, silicon source aorta, silicon source mucopolysaccharide, silicon source pectin, silicon source alginic acid, silicic acid, silanolate, silicon dioxide, and silica. More preferably, the dosage of silicon is about 10 mcg as sodium metasilicate.

Findings suggest that boron influences the metabolism of calcium, phosphorus, magnesium and cholecalciferol. Boron may also be involved in the functional efficiency of membranes. Preferably, the dosage of boron included is from about dosage 500 mcg to about 2000 mcg as calcium borogluconate, magnesium borogluconate, sodium borate, boric acid, potassium borate, sodium metaborage, boron proteinate, boron amino acid chelate, glyceroborate, magnesium perborate, sodium perborate, calcium perborate, and potassium perborate. Most preferably, however, the dosage of boron is about 1 mg as calcium borogluconate.

With regard to the vitamins and minerals included in the inventive formulation, each (with the possible exception of vitamin A, calcium, magnesium and biotin) is included in an amount equal to or greater than the minimum daily requirement in man. Further, it is preferred that the vitamins and minerals included in the inventive formulation are similar to those included in the multi-vitamin and mineral preparations Centrum® or One-A-Day® (as shown in Table 4).

TABLE 4

| CENTRUM ® | | | ONE-A-DAY | | |
|---|---|---|---|---|---|
| | Amount | % USRDA | | Amount | % USRDA |
| Vitamin | | | Vitamin | | |
| Vitamin A (as Acetate & Beta Carotene) | 5000 I.U. | 100% | Vitamin A (as Beta Carotene) | 5000 I.U. | 100% |
| | | | Vitamin A (as Acetate) | 1500 I.U. | 30% |
| Vitamin E (as DL-Alpha Tocopherol Acetate) | 30 I.U. | 100% | Vitamin E | 30 I.U. | 100% |
| Vitamin C (as Ascorbic Acid) | 60 mg | 100% | Vitamin C | 60 mg | 100% |
| Folic Acid | 400 mcg | 100% | Thiamine (B$_1$) | 1.5 mg | 100% |
| Vitamin B$_1$ (as Thiamine Mononitrate) | 1.5 mg | 100% | Riboflavin (B$_2$) | 1.7 mg | 100% |
| Vitamin B$_2$ (as Riboflavin) | 1.7 mg | 100% | Niacin | 20 mg | 100% |
| Niacinamide | 20 mg | 100% | Vitamin D | 400 I.U. | 100% |
| Vitamin B$_6$ (as Pyridoxine Hydrochloride) | 2 mg | 100% | Vitamin B$_6$ | 2 mg | 100% |
| Vitamin B$_{12}$ (as Cyanocobalamin) | 6 mcg | 100% | Folic Acid | 0.4 mg | 100% |
| Vitamin D | 400 I.U. | 100% | Vitamin B$_{12}$ | 6 mcg | 100% |
| Biotin | 30 mcg | 100% | Biotin | 30 mcg | 10% |
| Pantothenic Acid | 10 mg | 100% | Pantothenic Acid | 10 mg | 100% |
| Calcium (as Dibasic (elemental) Calcium Phosphate) | 162 mg | 16% | Iron | 18 mg | 100% |
| Mineral | | | Mineral | | |
| Phosphorus (as Dibasic Calcium Phosphate) | 125 mg | 13% | Calcium | 130 mg | 13% |
| Iodine (as Potassium Iodine) | 150 mcg | 100% | Phosphorus | 100 mg | 10% |
| Iron (as Ferrous Fumarate) | 18 mg | 100% | Iodine | 150 mcg | 100% |
| Magnesium (as Magnesium Oxide) | 100 mg | 25% | Magnesium | 100 mg | 25% |
| Copper (as Cupric Oxide) | 2 mg | 100% | Copper | 2 mg | 100% |
| Zinc (as Zinc Oxide) | 15 mg | 100% | Zinc | 15 mg | 100% |
| Manganese | 2.5 mg | * | Chromium | 10 mcg | * |
| Potassium (as Potassium Chloride) | 40 mg | * | Selenium | 10 mcg | * |
| Chloride (as Potassium Chloride) | 36.3 mg | * | Molybdenum | 10 mcg | * |

TABLE 4-continued

| | CENTRUM ® | | | ONE-A-DAY | |
|---|---|---|---|---|---|
| | Amount | % USRDA | | Amount | % USRDA |
| Chromium (as Chromium Chloride) | 25 mcg | * | Manganese | 2.5 mg | * |
| Molybdenum (as Sodium Molybdate) | 25 mcg | * | Potassium | 37.5 mg | * |
| Selenium (as Sodium Selenate) | 25 mcg | * | Chloride | 34 mg | * |
| Vitamin $K_1$ (as Phytonadione) | 25 mcg | * | | | |
| Nickel (as Nickel Sulfate) | 5 mcg | * | | | |
| Tin (as Stannous Chloride) | 10 mcg | * | | | |
| Silicon (as Sodium Metasilicate) | 10 mcg | * | | | |
| Vanadium (as Sodium Metavanadate) | 10 mcg | * | | | |

*No U.S. RDA established

It is known that certain amino acids are essential for proper cellular function. However, it has been suggested by researchers that select amino acids provide some protection against cancer, and may, in fact, act synergistically with the preferred antioxidants of the present invention to protect against cancer. Thus, it is one important aspect of the present invention to provide a daily dietary multi-vitamin and mineral supplement including antioxidants and select amino acids. According to one embodiment of the invention, the preferred antioxidants are selected from the group consisting of BHT, BHA, propyl gallate, and sodium benzoate, and the preferred amino acids or analogs are selected from the group consisting of glutathione, cysteine, methionine, glutamine, and taurine.

One preferred embodiment of the present invention provides a cancer-protective daily dietary multi-vitamin and mineral supplement including, in combination:
(a) from about 10 to about 300 mg of BHA or BHT;
(b) from about 10 to about 300 mg of propyl gallate;
(c) from about 10 to about 100 i.u. of vitamin E;
(d) from about 10 to about 1000 mg Vitamin C;
(e) from about 2500 to about 7500 i.u. of beta carotene; and
(f) from about 2 mcg to about 100 mcg of sodium selenate.

More preferably, however, the supplement includes:
from about 1000 to about 3000 i.u. of vitamin A;
from about 1 to about 300 mg of sodium benzoate;
from about 1 to about 20 mg of reduced L-glutathione;
from about 5 to about 100 mg of N-acetyl-L-cysteine;
from about 1 to about 20 mg of D,L-methionine;
from about 1 to about 20 mg of L-glutamine;
from about 1 to about 20 mg of taurine;
from about 10 to 100 mg of PABA;
from about 10 to about 1000 mg of polyunsaturated fatty acids having an EPA:DHA ratio of about 18:12;
from about 100 to about 300 i.u. of superoxide dismutase;
from about 2 to about 200 mg of a bioflavonoid;
from about 100 to about 300 i.u. of catalase;
from about 5 to about 100 mg of inositol; and
from about 10 to 500 mg of potassium sorbate or sorbic acid.

The inventive supplement includes many vitamins and minerals which are commonly used in commercially available multi-vitamin and mineral preparations. Preferably, the supplement of the present invention includes the following vitamins and minerals in an amount equal to or greater than the minimum daily requirement in man:
folic acid;
vitamin $B_1$;
vitamin $B_2$;
niacinamide;
vitamin $B_6$;
vitamin $B_{12}$;
vitamin $D_3$;
biotin;
pantothenic acid;
vitamin $K_1$;
calcium;
iodine;
potassium;
iron;
magnesium;
copper;
zinc;
manganese;
chromium;
molybdenum;
vanadium;
silicon; and
boron.

Most preferably, the present invention provides for a daily dietary supplement formulated as an oral sustained release tablet including, in combination:
about 50 mg of BHA or BHT;
about 50 mg of propyl gallate;
about 30 i.u of vitamin E;
about 250 mg of vitamin C;
about 5000 i.u of beta carotene;
sodium selenate sufficient to supply about 25 mcg of selenium;
about 2000 i.u of vitamin A acetate;

copper oxide sufficient to supply about 2 mg of copper;
zinc oxide sufficient to supply about 15 mg of zinc;
manganese gluconate sufficient to supply about 2 mg of manganese;
about 200 mg of polyunsaturated fatty acids having an eicosapentaenoic acid:docosahexenoic acid ratio of about 18:12;
about 50 mg of inositol;
about 40 mg of PABA;
about 50 mg of a bioflavonoid;
about 10 mg of reduced L-glutathione;
about 50 mg of N-acetyl-L-cysteine HCl;
about 200 mg of potassium sorbate or sorbic acid;
about 4 mg of sodium benzoate;
about 10 mg of taurine;
about 10 mg of L-methionine;
about 10 mg of L-glutamine;
about 200 i.u of superoxide dismutase from a food concentrate;
about 200 i.u of catalase from a food concentrate;
about 400 mcg of folic acid;
about 1.5 mg of vitamin $B_1$;
about 1.75 mg of vitamin $B_2$;
about 20 mg of niacinamide;
about 2 mg of vitamin $B_6$;
about 6 mcg of vitamin $B_{12}$;
about 600 iu of vitamin $D_3$;
about 30 mg of biotin;
about 10 mg of calcium pantothenate;
about 25 mcg of vitamin $K_1$;
about 100 mg of dicalcium phosphate;
potassium iodide sufficient to supply about 125 mg iodine;
potassium chloride sufficient to supply about 40 mg of potassium;
ferrous fumarate sufficient to supply about 20 mg of iron;
magnesium oxide sufficient to supply about 100 mg of magnesium;
chromium (+3)chloride sufficient to supply about 25 mcg of chromium;
sodium molybdate sufficient to supply about 25 mcg of molybdenum;
sodium metavanadate sufficient to supply about 10 mcg of vanadium;
sodium metasilicate sufficient to supply about 10 mcg of silicon;
about 2 mg of boron;
about 250 mg of calcium carbonate; and
about 100 mg of calcium citrate.

The formulations of the present invention contain a number of vitamins and minerals similar to other multivitamin formulations, e.g, Centrum®. However, the formulation of the present invention provides those vitamins and minerals in amounts which better reflect the scientific data concerning these agents. For example, the amount of vitamin A included in the present invention is less than in other available formulations because it can be toxic to older people. Further, the amount of beta-carotene included is greater because it is nontoxic and provides improved benefits. For the above reasons the vitamins and minerals included in the present invention offer a broader base of vitamins and minerals than presently available in the industry; thus, providing the public with a comprehensive multivitamin useful in the prevention of heart disease and cancer.

According to one preferred embodiment, the vitamins and minerals included in the inventive formulation are:

Vitamins (a) Vitamin A acetate from about 1000 to about 3000 iu;
(b) Beta carotene from about 3000 to about 6000 iu;
(c) Vitamin E, DL alpha tocopherol acetate from about 20 to about 40 iu;
(d) Calcium ascorbate from about 200 to about 400 mg;
(e) Folic acid from about 200 to about 600 mcg;
(f) Vitamin $B_1$ from about 1.0 to about 2 mg;
(g) Vitamin $B_2$ from about 1.5 to about 2 mg
(h) Niacinamide from about 10 to about 30 mg;
(i) Vitamin $B_6$ from about 1 to about 3 mg;
(j) Vitamin $B_{12}$ from about 4 to about 8 mcg;
(k) Vitamin $D_3$ from about 400 to about 800 iu;
(l) Biotin from about 20 to about 40 mcg;
(m) Calcium pantothenate from about 5 to about 15 mg; and
(n) Vitamin $K_1$ from about 15 to about 35 mcg.

Minerals (a) dicalcium phosphate from about 50 to about 150 mg;
(b) potassium iodide sufficient to supply from about 100 to about 150 mcg of iodine;
(c) potassium chloride sufficient to supply from about 20 to about 60 mg of potassium;
(d) ferrous fumarate sufficient to supply from about 16 to about 30 mg of iron;
(e) magnesium oxide sufficient to supply from 75 to about 12 omg of magnesium;
(f) copper oxide sufficient to supply from about 1 to about 3 mg of copper;
(h) zinc oxide sufficient to supply from about 10 to about 2 omg of zinc;
(i) manganese gluconate sufficient to supply from about 1 to about 3 mg of manganese;
(j) chromium (+3)chloride sufficient to supply from about 15 to about 35 mcg of chromium;
(k) sodium molybdate sufficient to supply from about 15 to about 35 mcg of molybdenum;
(l) sodium selenate sufficient to supply from about 15 to about 35 mcg of selenium;
(m) sodium metavanadate sufficient to supply from about to about 15 mcg of vanadium;
(n) sodium metasilicate sufficient to supply from about 5 to about 15 mcg of silicon; and
(o) boron from about 1 to about 3 mg.

It should be noted, however, that other vitamins and minerals not listed above may be added to the formulations of the present invention without departing from the spirit of the present invention.

However, according to the most preferred embodiment, the vitamins and minerals of the present invention include:

Vitamins (a) about 2000 iu of vitamin A acetate;
(b) about 5000 iu of beta carotene;

(c) about 30 iu of vitamin E, DL alpha tocopherol acetate;
(d) about 250 mg of calcium ascorbate;
(e) about 400 mcg of folic acid;
(f) about 1.5 mg of vitamin $B_1$;
(g) about 1.75 mg of vitamin $B_2$;
(h) about 20 mg of niacinamide;
(i) about 2 mg of vitamin $B_6$;
(j) about 6 mcg of vitamin $B_{12}$;
(k) about 600 iu of vitamin $D_3$;
(l) about 30 mg of biotin;
(m) about 10 mg of calcium pantothenate; and
(n) about 25 mcg of vitamin $K_1$.

Minerals (a) about 100 mg of dicalcium phosphate;
(b) potassium iodide sufficient to supply about 125 mg iodine;
(c) potassium chloride sufficient to supply about 40 mg of potassium;
(d) ferrous fumarate sufficient to supply about 20 mg of iron;
(e) magnesium oxide sufficient to supply about 100 mg of magnesium;
(f) copper oxide sufficient to supply about 2 mg of copper;
(h) zinc oxide sufficient to supply about 15 mg of zinc;
(i) manganese gluconate sufficient to supply about 2 mg of manganese;
(j) chromium (+3)chloride sufficient to supply about 25 mcg of chromium;
(k) sodium molybdate sufficient to supply about 25 mcg of molybdenum;

| | |
|---|---|
| (l) | sodium selenate sufficient to supply about 25 mcg of selenium; |
| (m) | sodium metavanadate sufficient to supply about 10 mcg of vanadium; |
| (n) | sodium metasilicate sufficient to supply about 10 mcg of silicon; and |
| (o) | about 2 mg of boron. |

The protective agents included in the inventive formulations are either already approved by the FDA or generally regarded as safe (GRAS) by the FDA or are generally thought to be safe by scientific experts. These agents include antioxidants, amino acids, and enzymes, which have been shown to be effective in preventing the induction of cancer and cardiovascular disorders as well as extending the life span of experimental animals. Further, a number of the ingredients have been shown to act synergistically with other agents in the formulation. This combined effect should increase their protective effects. For example, selenium and vitamin E work synergistically against the induction of breast cancer. Further, in a number of studies, BHA when given with vitamin A, beta-carotene and vitamin E was shown to provide a protection against cancer. Accordingly, the present invention is directed to a multi-vitamin dietary supplement formulation, and methods for producing and administering the same to an individual in need thereof. It is demonstrated that the present invention provides a formulation which inhibits tumor-promoting effects of carcinogens.

A further aspect of the present invention is directed to a method for producing the formulations of the present invention. Preferably, the formulation is tableted, and most preferably, the formulation is tableted as a sustained release tablet. The sustained release tablets of the present invention are intended to provide for the extended action of the ingredients from a single dose. Thus, the sustained released tablet is a convenient dosage form by virtue of eliminating the necessity for dosage several times during the day. Moreover, therapeutic benefits may also be obtained by the sustained release of the active ingredients of the inventive formulation. It is believed desirable that the sustained release dosage form of the present invention will provide a slow and constant supply of antioxidants, amino acids, and other beneficial dietary supplements which will provide protection against cancer and cardiovascular disease throughout the day.

In order to stabilize the preparations of the present invention, it has been determined that several of the more reactive constituents are preferably microencapsulated. The microencapsulation of select constituents prevents those constituents from reacting with other ingredients if left unchecked, which would shorten the shelf life of a commercial product embodying the inventive formulation. According to one embodiment, the preferred sulfur-containing amino acids and the polyunsaturated acids are microencapsulated. More specifically, glutathione and omega-3 fish oil are preferably microencapsulated when included in the invented formulation.

Microencapsulation is effected by, for example, spray drying the ingredient with a food grade wax or saturated oil which coats the ingredients, forming particles or microspheres (Luzzi, L. A. *J. Pharmaceutical Sciences*, 59:1367–1376, 1970). A gelatin or gum coating may also be used.

According to one preferred embodiment, hydroxypropyl methylcellulose is used as a pharmaceutical adjunct which provides a sustained release of the active constituents of the tablet. According to this preferred embodiment, based upon the physical parameters involved in formation of a tablet which is determined by the nature of the ingredients (compressibility, adhesion of particles, etc.), up to 20% of the dry weight could be required for hydroxypropyl methylcellulose to ensure proper time release tablet. Thus, according to one embodiment, a total formulation weight, including time released material, would have a weight of about 1.15 g/tablet. Because of the bulk of the formulation, the formulation is preferably produced and administered as 1–3 tablets daily.

The following examples are presented to describe specific preferred embodiments and utilities of the present invention and are not meant to limit the present invention unless otherwise stated in the claims appended hereto.

EXAMPLES

In vitro Disintegration Characteristics

A comparison was made between the relative disintegrations of Centrum tablets and the sustained release tablets of the present invention.

Figure 1:
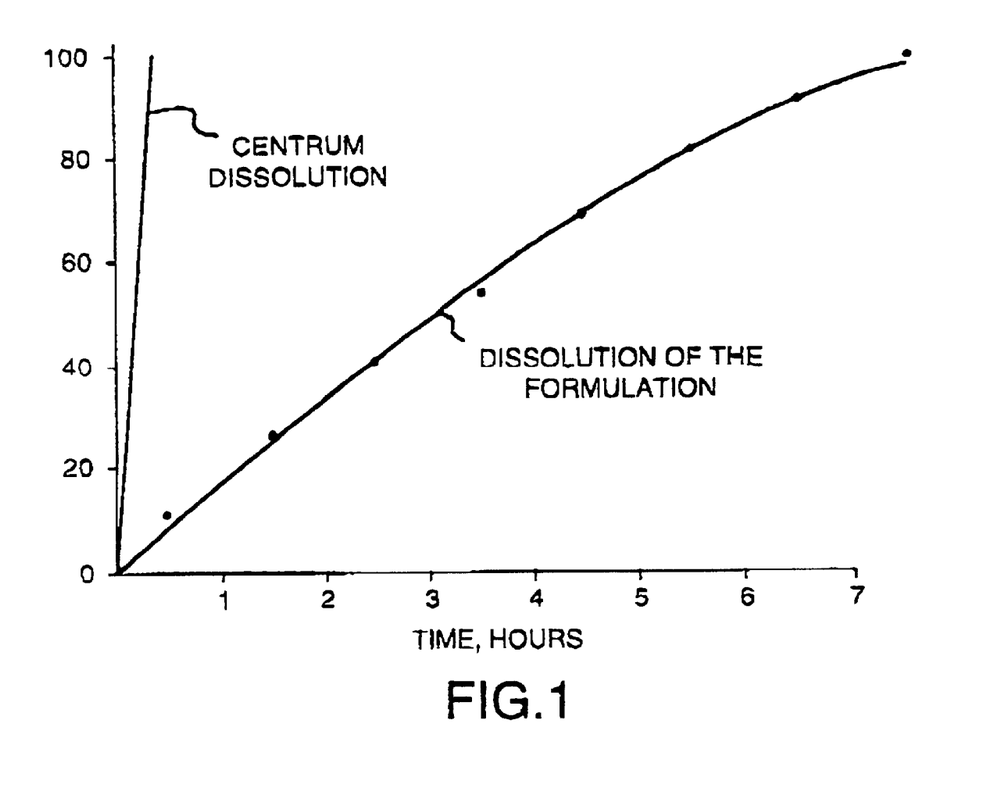
FIG. 1 graphically represents, as a function of % potassium released versus time, the dissolution of Centrum tablets in gastric juice as compared to the tablets of the present formulation.
Figure 2:
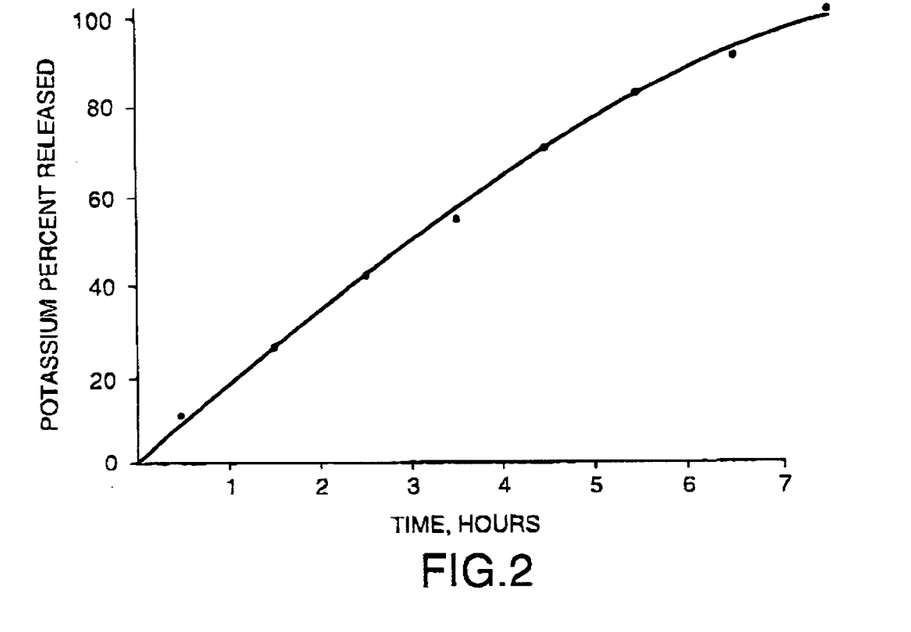
FIG. 2 graphically represents, as a function of % potassium released versus time, the dissolution of the sustained release tablets of the present invention in intestinal juice.
Figure 3:
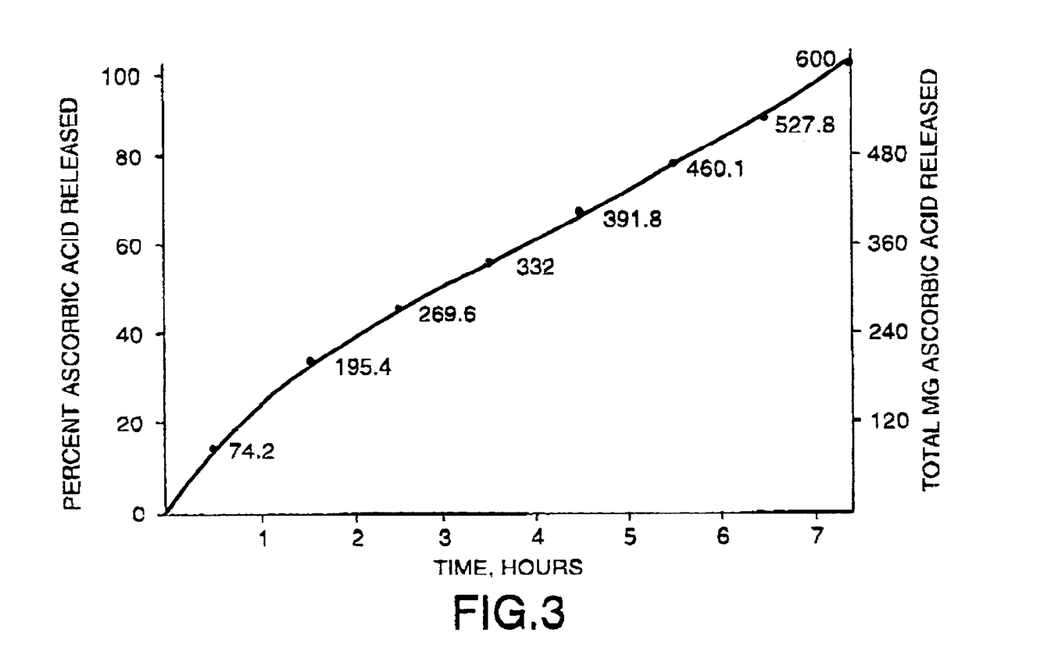
FIG. 3 graphically represents, as a function of % ascorbic acid released versus time, the dissolution of the sustained release tablets of the present invention in intestinal juice.
Figure 4:
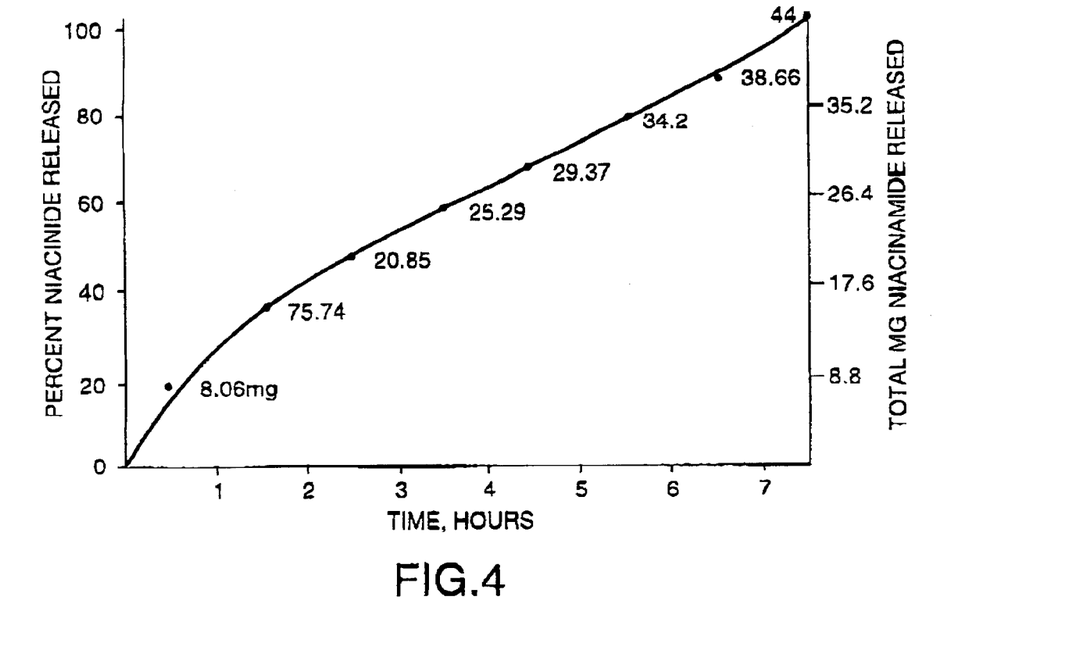
FIG. 4 graphically represents, as a function of % niacinamide released versus time, the dissolution of the sustained release tablets of the present invention in intestinal juice.
Figure 5:
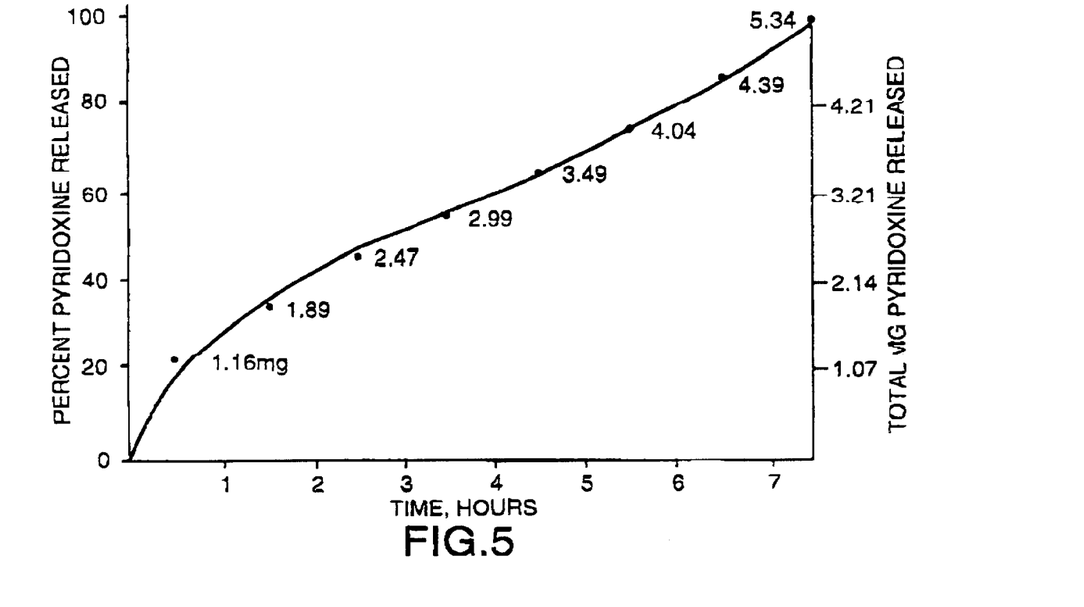
FIG. 5 graphically represents, as a function of pyridoxine % released versus time, the dissolution of the sustained release tablets of the present invention in intestinal juice.

As a measurement of disintegration, the release of four different vitamins, potassium, vitamin C, niacinamide, and pyridoxine was measured. The results, summarized in FIGS. 1–6, show that the sustained release tablet of the present invention provides for uniform disintegration over at least seven hours.

As a general procedure, gastric and intestinal juices were prepared according to the United States Pharmacopeia XVIII. The dissolution tests were conducted using the apparatus specified for such procedures in the National Formulary XIII. The apparatus generally consisted of a horizontal rotating shaft to which was attached clamps for holding round cylinders approximately 150 mm long and having a diameter of approximately 30 mm wherein the tablets were contained. The apparatus then submerges the tablets in the appropriate dissolution fluid. The temperature of the dissolutions fluid was maintained at 37±2° C. throughout the study. Eight tablets were used to generate the dissolution data. Six Centrum (UDC0005-4239-13 Lederle Laboratories Division American Cyanamid Company) and two sustained release tablets of the present invention, which were prepared as follows.

The following shows the content and instructions for preparing a most preferred formulation (300,000 tablets 3 tablet/dose) of the present invention.

| Weight Range Per Dose (dose = 1 day supply) | Vitamins | Grams |
|---|---|---|
| 5.4 mg | Vitamin A acetate 2000 iu from 500,000 iu/gm beadlets with 35% overage | 540 |
| 40.5 mg | Beta carotene 5000 iu = 30 mg with 35% overage from 10% beadlets | 405 |
| 231 mg | Vitamin E DL alpha tocopherol acetate 100 iu from 50% 2.1 mg finished material with 10% overage | 23,100 |
| 300 mg | Calcium ascorbate = 250 mg with 20% overage | 30,000 |
| 5 mg | Folic acid as 10% trit = 400 mcg/dose with 25% overage | 500 |
| 1.73 mg | Vitamin $B_1$ dose = 1.5 mg with 15% overage | 173 |
| 1.87 mg | Vitamin $B_2$ dose = 1.7 mg with 10% overage | 187 |
| 22 mg | Niacinamide dose = 20 mg with 10% overage | 2,200 |
| 2.67 mg | Vitamin $B_6$ dose = 2 mg with 10% overage | 267 |
| 0.75 mg | Vitamin $B_{12}$ dose = 6 mcg from 1% trit on resin with 25% overage | 75 |
| 8.1 mg | Vitamin $D_3$ dose = 600 iu from 100,000 iu/gm with 35% overage | 810 |
| 3.3 mg | Biotin dose = 30 mcg from 1% trit with 10% overage | 330 |
| 14 mg | Calcium pantothenate dose = 10 mg with 30% overage | 1,400 |
| 3.4 mg | Vitamin $K_1$ dose = 25 mcg from 1% trit with 35% overage | 340 |
| 100 mg | Dicalcium phosphate dihydrate (use in granulations) | 10,000 |
| 0.20 mg | Potassium iodide supplies 150 mcg iodine | 20[1] |
| 76.3 mg | Potassium chloride supplies 40 mg potassium | 7,630 |
| 155 mg | Ferrous gluconate supplies 18 mg iron | 15,550 |
| 166 mg | Magnesium oxide supplies 100 mg magnesium | 16,660 |
| 2.503 mg | Copper oxide supplies 2 mg copper | 250 |
| 18.75 mg | Zinc oxide supplies 15 mg zinc | 1,875 |
| 22.7 mg | Manganese gluconate supplies 2.5 mg manganese | 2,270 |
| 0.08 mg | Chromium (+3) chloride supplies 25 mcg chromium | 8[2] |
| 0.06 mg | Sodium molybdate supplies 25 mcg molybdenum | 6[3] |
| 0.06 mg | Sodium selenate supplies 25 mcg selenium | 6[4] |
| 0.038 mg | Sodium metavanadate supplies 10 mcg vanadium | 3.8[6] |
| 0.044 mg | Sodium metasilicate supplies 10 mcg silicon | 4.4[5] |
| 22.3 mg | Calcium borogluconate supplies 1 mg boron | 2,230 |
| 100 mg | Citrus bioflavonoids from 50% material supplying 50 mg per dose | 10,000 |
| 4 mg | Sodium benzoate | 400 |
| 250 mg | Calcium carbonate | 25,000 |
| 100 mg | Calcium citrate | 10,000 |
| 10 mg | L-glutathione (reduced) (microencapsulated) | 1,000 |
| 50 mg | N-acetyl-L-cysteine HCl | 51000 |
| 200 mg | Potassium sorbate/sorbic acid | 20,000 |
| 40 mg | PABA | 4,000 |
| 50 mg | BHA or | 5,000 |
| 50 mg | BHT | 5,000 |
| 571 mg | Omega 3 fish oils supplying 200 mg Omega 3 oils from microencapsulated material which is 35% Omega 3 having an EPA:DHA ratio of 18:12 | 57,100 |
| 50 mg | Inositol | 5,000 |
| 150 mg | Vegetable source SOD 200 units (mfu) Vegetable source catalase 200 units (bsu) | 15,000 |
| 50 mg | Propyl gallate | 5,000 |
| 10 mg | Taurine | 1,000 |
| 10 mg | DL methionine | 1,000 |

-continued

| Weight Range Per Dose (dose = 1 day supply) | Vitamins | Grams |
|---|---|---|
| 10 mg | L glutamine | 1,000 |
| | hydroxypropylmethylcellulose (e.g. Methocel K, Dow Chem.) | 61,162 |
| | Magnesium Stearate | 1,500 |
| | Total weight of ingredients = 345,002 | |
| | Tablet Weight = 1.15 grams | |

[1] The KI was dissolved in 50 ml $H_2O$ with about 2000 gm of the dicalcium phosphate dihydrate. The mixture was dried at 120° F. for 48 hours and then milled.
[2] The $CrCl_3$ was also dissolved in 50 ml $H_2O$ with about 2000 gms dicalcium phosphate dihydrate. This mixture was also dried at 120° F. for about 48 hours and was then milled.
[3] The sodium molybdate was dissolved in 50 ml $H_2O$ with about 2000 gm of dicalcium phosphate dihydrate. The mixture was dried at 120° F. for about 48 hours and then milled.
[4] The sodium selenate was dissolved in 50 ml $H_2O$ with 2000 gms dicalcium phosphate dihydrate and dried at 120° F. for about 48 hours and then was milled.
[5] The sodium metasilicate was mixed with 2000 gms dicalcium phosphate dihydrate and added to the sodium metavandate[6] which was dissolved in 50 ml $H_2O$. This mixture was then dried at 120° F. for about 48 hours and then was milled. All of the above milled ingredients were then mixed.

All the remaining ingredients were weighed separately and added to a stainless steel ribbon blender and blended for 10 minutes. Tablets were then compressed on a rotary tablet press machine. Tablets weighed 1.1667 grams±2%. The tablets were oblong measuring 0.75 inches (height)×0.35 inches (width)×0.30 inches (depth). The tablets were produced at 4 tons pressing force per square inch. It was determined that these tablets disintegrated uniformly over an 8 hour period. The tablets are also suitable for an aqueous film coating, such as with riboflavin, in a conventional film coating pan.

The dissolution data were collected at ½ hr, 1 and ½ hr, 2 and ½ hr, 3 and ½ hr, 4 and ½ hr, 5 and ½ hr, 6 and ½ hr, and 7 and ½ hr. Data for Centrum were obtained for 6 tablets under identical conditions. However, the total dissolution occurred for Centrum at approximately 20 minutes. Therefore, Centrum was only observed in gastric test solution. These data are summarized in FIG. 1.

The release of potassium from the tablet of the present invention was monitored using a Perkin Elmer spectrophotometer. To do this monobase sodium phosphate was used in place of $H_2KPO_4$ in the intestinal liquid. Replacement of $H_2KPO_4$ with $H_2NaPO_4$ allowed accurate measurement of potassium from the tablet without interferences.

Measurements of potassium were made at 766.5 lambda using atomic absorption. Results:

| Time | % K released during observed interval |
|---|---|
| 0–½ hr | 11.54 |
| ½–2½ hr | 14.61 |
| ½–2½ hr | 14.61 |
| 2½–3½ hr | 14.61 |
| 3½–4½ hr | 13.15 |
| 4½–5½ hr | 13.15 |
| 5½–6½ hr | 10.96 |
| 6½–7½ hr | 7.30 |

To obtain interval values intestinal fluid was replaced hourly. The above data are summarized in FIG. 2.

Data for ascorbic acid, niacinamide, and pyridoxine HCl were generated using a Bausch and Lomb spectrophotometer (Model 21). The wavelengths used for analysis were:

| | |
|---|---|
| 245 nm | Ascorbic Acid |
| 261 nm | Niacinamide |
| 291 nm | Pyridoxine |

Samples were taken from ½ hr, ½ hr, 2½ hr, 3 ½ hr, 4½ hr, 5½ hr, 6½ hr, 7½ hr periods. These data are summarized in FIGS. 3, 4, and 5 respectively. The data collected show that the tablet of the present invention provides for the sustained release of the constituents of the inventive formulation.

While the invention is susceptible to various modifications and alternative forms, a specific embodiment thereof has been shown by way of example and therein was described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A method of inhibiting two-stage skin carcinogenesis—promoting effects of carcinogenesis in an animal, the method comprising administration of prophylactically effective amounts of a dietary supplement to an animal, wherein the supplement includes: BHA or BHT; vitamin E; and β-carotene.

2. The method of claim 1, wherein the supplement is further defined as comprising:

from about 10 to about 300 mg BHA or BHT;
from about 10 to about 100 I.U. of vitamin E; and
from about 2500 to about 7500 I.U. of β-carotene.

3. The method of claim 1, wherein the supplement is further defined as comprising:

about 50 milligrams of BHA or BHT;
about 100 I.U. of vitamin E; and
about 5000 I.U. of β-carotene.

4. The method of claim 1, wherein the administration is daily.

* * * * *